United States Patent [19]
Holzner

[11] Patent Number: 5,858,958
[45] Date of Patent: Jan. 12, 1999

[54] USE OF A 4-TERT-BUTYL-1-CYCLOHEXANOL AS AN ANTIOXIDANT

[75] Inventor: Günter Holzner, Grand-Lancy, Switzerland

[73] Assignee: Firmenich SA, Geneva, Switzerland

[21] Appl. No.: 875,887

[22] PCT Filed: Dec. 6, 1996

[86] PCT No.: PCT/IB96/01370

§ 371 Date: Aug. 6, 1997

§ 102(e) Date: Aug. 6, 1997

[87] PCT Pub. No.: WO97/22332

PCT Pub. Date: Jun. 26, 1997

[30] Foreign Application Priority Data

Dec. 19, 1995 [CH] Switzerland ............................ 3579/95

[51] Int. Cl.[6] ................................ C11D 3/20; C11D 3/50; C11D 9/60; C11D 10/06
[52] U.S. Cl. .......................... 510/505; 510/119; 510/129; 510/130; 252/407
[58] Field of Search ...................................... 510/119, 129, 510/130, 158, 159, 434, 489, 505; 252/397, 399, 407

[56] References Cited

U.S. PATENT DOCUMENTS

| | | |
|---|---|---|
| 5,107,038 | 4/1992 | Weinstein . |
| 5,160,498 | 11/1992 | Weinstein . |
| 5,668,094 | 9/1997 | Bacon et al. ............................. 510/101 |
| 5,670,475 | 9/1997 | Trinh et al. ............................. 510/470 |

FOREIGN PATENT DOCUMENTS

| | | |
|---|---|---|
| 129980 | 2/1985 | European Pat. Off. . |
| 596493 | 11/1994 | European Pat. Off. . |
| 07-291809 | 11/1995 | Japan . |
| 97/30688 | 8/1997 | WIPO . |
| 97/30689 | 8/1997 | WIPO . |
| 97/31094 | 8/1997 | WIPO . |
| 97/31097 | 8/1997 | WIPO . |

*Primary Examiner*—Paul Lieberman
*Assistant Examiner*—John M. Petruncio
*Attorney, Agent, or Firm*—Pennie & Edmonds LLP

[57] ABSTRACT

The use of 4-tert-butyl-1-cyclohexanol as an antioxidant in soaps, shampoos and other cosmetic products, as well as in all-purpose cleaners, is described.

4 Claims, No Drawings

USE OF A 4-TERT-BUTYL-1-CYCLOHEXANOL AS AN ANTIOXIDANT

TECHNICAL FIELD AND PRIOR ART

The present invention relates to perfumery and cosmetics. It concerns, more particularly, the use of 4-tert-butyl-1-cyclohexanol as antioxidant.

4-Tert-butyl-1-cyclohexanol is a known perfuming ingredient but which is not used very currently in perfumery as a result of its not too elegant camphoraceous note. It develops in fact an odor of the woody-patchouli, camphoraceous type. It is also known that this compound is very stable even in very aggressive media characteristic of soaps, detergents or bleaching products. However, to our knowledge, it has never been suggested to use this compound as a stabilising agent against oxidation in cleaning or cosmetic products.

DESCRIPTION OF THE INVENTION

We have now discovered that 4-tert-butyl-1-cyclohexanol turns out to be very efficient as an antioxidant, namely when used in detergent and cosmetic media containing fat materials which are easily oxidised upon exposure to air and/or light and the oxidation products of which develop unpleasant odors, particularly of the rancid type.

It is known, for example, that certain types of soaps develop rancid, piquant and fruity odors after only a few weeks of storage in air. Now, we have observed that occurrence of such malodors could be entirely prevented, or at least prevented for far longer storage periods, if 4-tert-butyl-1-cyclohexanol was added to these soaps.

Similar effects were observed in shampoos or yet in bath or shower gels.

In a general manner, this compound reveals itself as an efficient stabilising agent against oxidation in all the cosmetic and skin or hair cleansing products comprising materials which are susceptible of being oxidised by air and/or light exposure and, as a result, of developing unpleasant odors. In this context, one can cite, in addition to the consumer products mentioned above, cosmetic creams and milks.

It has also been established that this compound could be useful as an anti-oxidant in other cleaning or detergent products, particularly general use detergents or all-purpose cleaners for hard surfaces, dishwashing products and other, whenever they comprise fat materials susceptible of being oxidised upon exposure to air or light.

To achieve the effects desired according to the invention, 4-tert-butyl-1-cyclohexanol can be added to the soap, shampoo or other type base either on its own or in admixture with other ingredients of current use in perfumery, namely usual perfuming co-ingredients, solvents or adjuvants. A more detailed description of the latter is here superfluous. Their nature will depend namely of the perfuming effect one wants to achieve, as well as on the type of product to be perfumed, and the skilled person is able to choose such ingredients on the basis of her general knowledge in the art and taking inspiration from reference textbooks such as the book of S. Arctander, Perfume and Flavor Chemicals, Montclair, N.J. (1969) or more recent versions thereof, amongst others.

The concentrations in which the above-mentioned compound can be added to the various products to impart its anti-oxidation effect vary in a wide range of values. Beneficial effects can already be observed at concentrations of the order of 0.005 or 0.01% by weight, relative to the weight of the finished product, i.e. soap, shampoo, shower gel or other. However, it is preferred according to the invention to use this compound in concentrations of, or above, 0.05% by weight, relative to the weight of the finished product. More preferably, such products will contain in the order of 0.05 to 0.5% by weight of 4-tert-butyl-1-cyclohexanol.

As is apparent from the examples presented further on, 4-tert-butyl-1-cyclohexanol reveals itself as a more efficient antioxidant than other agents currently used for this purpose, such as BHT (2,6-di-tert-butyl-p-cresol; origin: Bayer), α- or γ-tocopherol, ascorbic, citric or tartaric acids and their salts or esters, or yet any mixtures of two or more of these products. It goes without saying that 4-tert-butyl-1-cyclohexanol can also be used in admixture with these antioxidants. We observed in particular that excellent results could be obtained when 4-tert-butyl-1-cyclohexanol was used in combination with the tocopherols (α- or γ), citric acid, ascorbic acid or tartaric acid or yet their esters.

As has been cited above, 4-tert-butyl-1-cyclohexanol can be used as antioxidant in perfuming or cosmetic compositions, in compositions for cleaning skin or hair, or yet in all-purpose cleaning compositions, and the invention also concerns such compositions.

The nature of the base compositions to which this compound is added is quite immaterial here, all the soap, cosmetic or detergent type bases currently used in the corresponding industries or known in the art being convenient for preparing compositions according to the invention wherein 4-tert-butyl-1-cyclohexanol is incorporated as antioxidant. The examples of such base compositions presented hereafter are cited for illustrative purposes only and it is clear that other current bases of similar type, containing materials susceptible of being oxidised, can be used instead of those here given as examples.

In particular, the cosmetic and skin or hair cleaning compositions which contain 0.05 to 0.5% by weight of this compound, relative to the weight of the composition, are preferred according to the invention. The soaps, shampoos or yet the shower or bath gels are embodiments of such compositions according to the invention, and the same applies to the nourishing or beauty creams or milks, or other.

Moreover, it is to be noted that it is a known fact that, in certain media where hydrolysis occurs readily, the addition thereto of 4-tert-butyl-1-cyclohexyl acetate can be equivalent to adding 4-tert-butyl-1-cyclohexanol, said acetate being susceptible of being partially or totally hydrolysed to form this corresponding alcohol. It goes therefore without saying that the invention also relates to any compositions or products of the type above-mentioned which contain, or to which there is added, said 4-tert-butyl-1-cyclohexyl acetate, and the pH of which is susceptible of causing the formation therefrom of the corresponding 4-tert-butyl-1-cyclohexanol, in an amount sufficient for the latter to impart its antioxidant effect to the composition or product.

When used in perfuming compositions, which can themselves be added to the above-mentioned products to impart thereto certain fragrances, 4-tert-butyl-1-cyclohexanol can make up 5 to 50% of the weight of the perfuming composition.

The invention will now be described in more detail by way of the following examples, wherein the temperatures are indicated in degrees Celsius.

EMBODIMENTS OF THE INVENTION

EXAMPLE 1

Stabilisation of a Semi-synthetic Type Soap

A soap base was prepared by admixture of the following ingredients, according to current methods.

| Ingredients | % by weight |
|---|---|
| Sodium cocoylisethionate[1] | 51.0 |
| Sodium dodecylbenzenesulfonate[2] | 2.0 |
| Sodium isethionate[3] | 5.0 |
| Stearic acid | 25.0 |
| Sodium salt of $C_{12}$ to $C_{18}$ fatty acids | 17.0 |
| Total | 100.0 |

[1] origin: PPG Industries, USA
[2] origin : Chem. Werke Hüls, Germany
[3] origin: Witco Chem. Comp., USA To this base composition there were added the ingredients cited in the table hereafter, in the amounts indicated, to prepare samples of stabilised soap bases.

TABLE I

| | Sample % by weight, relative to the base | | | | |
|---|---|---|---|---|---|
| Ingredients | A | B | C | D | E |
| Tenox ®[1] GTII | — | 0.07 | — | 0.05 | — |
| Irganox ®[2] PS-800 | 0.05 | — | 0.05 | 0.05 | — |
| Citric acid* | 0.2 | 0.2 | 0.2 | 0.2 | 0.2 |
| BHT | 0.07 | — | 0.07 | — | — |
| Turpinal ®[3] SL | — | — | 0.1 | — | — |
| 4-tert-butyl-1-cyclohexanol | — | — | — | 0.1 | 0.2 |

*50% in water
[1] α-tocopherol; origin: Eastman Chemicals
[2] dilaurylthiodipropionate; origin: Ciba-Geigy AG
[3] etidronic acid; origin: Henkel Soaps were stamped with these stabilised bases in the conventional manner. Soaps A to E thus obtained were stored in glass containers, at 40° and then subjected to evaluation by a panel of expert perfumers, on a blind test.

The panel judged that soaps A to C developed a fatty, butter and rancid odor, which could not be found in soap D, nor in soap E, both of which, furthermore, presented a slightly floral fragrance.

EXAMPLE 2

Stabilisation of Solid Soaps

A stabilising mixture was prepared by means of 1 g of 4-tert-butyl-1-cyclohexanol, 0.5 g of Tenox® GT II and 0.5 g of Irganox® PS-800.

By means of the base composition described in example 1, perfumed soap bases were then prepared, by adding the ingredients indicated hereafter, in the amounts cited:

TABLE II

| | Sample % by weight, based on the weight of the base composition | | | | |
|---|---|---|---|---|---|
| Ingredients | A | B | C | D | E |
| Hedione ®[1] | 0.05 | 0.05 | 0.05 | 0.05 | 0.05 |
| Rosewood essential Oil | 0.1 | — | — | — | — |
| Bergamot essential oil | — | 0.1 | — | — | — |
| Benzoin essential oil* | — | — | 0.1 | — | — |
| Cedar essential oil | — | — | — | 0.1 | — |
| Geranium essential oil | — | — | — | — | 0.1 |

*at 20% in dipropyleneglycol
[1] methyl dihydrojasmonate; origin: Firmenich SA, Geneva, Switzerland Soaps A to E were stamped with these soap bases. At the same time, soaps A' to E' were obtained from the bases A to E, but to which there had been further added 0.3% of the stabilising mixture cited above.

These ten soaps were stored at 40° during one month and then evaluated on a blind test and two by two, i.e. A and A', B and B', etc . . . , by a panel of experts.

The result of these evaluations showed that soaps A' to E' had a good odor, without any fatty, rancid note, whereas soaps A to E developed fragrances in which the unpleasant rancid notes were clearly detected.

EXAMPLE 3

Stabilisation of Solid Soaps

A standard soap base was prepared in a conventional manner by admixing the following ingredients:

| Ingredients | % by weight |
|---|---|
| Sodium salts of beef tallow fatty acids | 60.0 |
| Sodium salts of coconut oil fatty acids | 26.0 |
| Water | 14.0 |
| Total | 100.0 |

To this soap base there was then added 1.5 to 2% by weight of one of the perfuming compositions A or B containing the following ingredients, to prepare perfumed soap bases:

| Ingredients | Composition A (Parts by weight) | Composition B (Parts by weight) |
|---|---|---|
| Phenethylol | 3500 | 3500 |
| Citronellol | 2000 | 2000 |
| Iralia ®[1] | 300 | 300 |
| Geraniol | 600 | 600 |
| Diphenyl ether | 200 | 200 |
| Benzyl acetate | 800 | 800 |
| Phenylethyl acetate | 400 | 400 |
| 3-Methyl-5-phenyl-1-pentanol[2] | 400 | 400 |
| Dorinia SA[3] | 100 | 100 |
| Vert de lilas[4] | 200 | 200 |
| 50%* 15-Pentadec-(11,12)-enolide[5] | 50 | 50 |
| 4-tert-Butyl-1-cyclohexanol | — | 1000 |
| Total | 9000 | 10000 |

*in dipropyleneglycol
[1] methylionone; origin: Firmenich SA, Geneva, Switzerland
[2] origin: Firmenich SA, Geneva, Switzerland
[3] origin: Firmenich SA, Geneva, Switzerland
[4] (2,2-dimethoxyethyl)benzene; origin: Givaudan-Roure, Vernier, Switzerland
[5] origin: Firmenich SA, Geneva, Switzerland Soaps A and B were conventionally stamped with the soap bases perfumed by means of the compositions A, respectively B.

After storage for a month at 40°, the two soaps were evaluated by a panel of expert perfumers, on a blind test. In the opinion of the latter, soap B developed a floral, rose, green, musky type odor, whereas soap A presented clearly detectable fatty, rancid notes, which rendered its odor distinctly less pleasant than that of soap B.

EXAMPLE 4

Preparation of a Liquid Shampoo

A liquid shampoo, intended for body and hair cleaning, was prepared by admixing the following ingredients, according to the usual techniques:

| Ingredients | % by weight |
| --- | --- |
| Texapon ®[1] N28 | 25.0 |
| Medialan ®[2] LD | 7.0 |
| Demineralised water | 64.4 |
| NaCl | 1.5 |
| Citric acid | 0.5 |
| Kathon ®[3] CG | 0.1 |
| Comperland ®[4] KD | 1.5 |
| Total | 100.0 |

[1] sodium ethersulfate; origin: Henkel
[2] lauryl sarcosinate; origin: Hoechst
[3] preserver; origin: Röhm & Haas
[4] coconut acid diethanolamide; origin: Henkel To this unfragranced base shampoo there were added 0.1% by weight of 4-p-tert-butyl-1-cyclohexanol, 0.05% by weight of Tenox® GII, 0.05% by weight of Irganox® PS-800 and 0.1% by weight of citric acid, to obtain a stabilised shampoo. Separate plastic containers were filled with this stabilised shampoo and with the base shampoo.

After storing for one month at 40°, the two shampoos were evaluated by a panel of experts, on a blind test. The latter indicated a marked preference for the stabilised shampoo, which presented no traces of fatty odor notes, whereas the base shampoo had a well marked acrid and fat odor.

EXAMPLE 5

Stability Test

In order to test the antioxidant effect of 4-tert-butyl-1-cyclohexanol in perfuming compositions susceptible of air oxidation, there was added to a mixture of orange terpenes (containing 95% by weight of limonene), 0.1% by weight of the above-mentioned cyclohexanol, 0.05% by weight of Irganox® PS-800 and 0.05% by weight of Tenox® GT II.

The mixture of terpenes on their own, and the mixture of terpenes with the above-mentioned stabilising compounds, were subjected to a Rancimat type test (see for example, M. W. Läubli, Lebensmittelchemie 48, page 134). In order to do this, the two mixtures were heated to 110°, under air, while measuring their conductivity. It was thus observed that the conductivity of the unstabilised mixture of terpenes indicated its oxidation after 2 h of heating, whereas the terpene mixture which contained the stabilising agents only started to show oxidation after 5.5 h of heating in air.

EXAMPLE 6

Stabilisation of an All-purpose Cleaner

An all-purpose cleaner was prepared by admixing the following ingredients, according to the usual art methods.

| Ingredients | % by weight |
| --- | --- |
| Water | 74.7 |
| Sodium carbonate | 3.0 |
| Sodium citrate | 2.0 |
| Sodium cumolsulfonate[1] | 7.0 |
| Marlon ®[2] A 375 | 10.0 |
| Tergitol ®[3] 15-S-9 | 3.0 |
| Perfume[4] | 0.3 |
| Total | 100.0 |

[1] origin: Hüls AG, Germany
[2] sodium dodecylbenzene sulfonate; origin: Huls AG, Germany
[3] $C_{11}$–$C_{15}$ ethoxylated secondary alcohol; origin: Union Carbide, USA
[4] Blue Water, n° 114338; origin: Firmenich SA, Geneva, Switzerland To this perfumed base composition, there was then added 0.1% by weight of sweet almond oil to obtain an all-purpose cleaner base. With the latter there was then prepared a novel cleaning composition according to the invention via addition of 0.2% by weight of 4-tert-butyl-1-cyclohexanol. The all-purpose cleaner base and the novel all-purpose cleaner were then stored, in plastic bottles, under ultraviolet light during 8 h. At the end of this storage period, both bottles were evaluated, on a blind test, by a panel of experts, who indicated that the product containing 4-tert-butyl-1-cyclohexanol presented no traces of any fatty notes, whereas the base detergent had a rancid almond oil odor.

What is claimed is:

1. A composition comprising a cosmetic, cleansing or perfuming ingredient of an oxidizable fat material that is subject to oxidation by air, light, or both air and light; 4-tert-butyl-1-cyclohexanol in an amount effective to act as an antioxidant for the oxidizable fat material of the composition; and at least one compound selected from the group consisting of α-tocopherol, γ-tocopherol, ascorbic acid, citric acid, tartaric acid and esters thereof, in an amount effective to act as a further antioxidant for the oxidizable fat material of the composition, wherein the composition is substantially free of oxidizing agents.

2. The composition of claim 1 specifically in the form of a perfuming composition, wherein the amount of 4-tert-butyl-1-cyclohexanol is 5 to 50% by weight of the perfuming composition.

3. The composition of claim 1 specifically in the form of a cosmetic composition, a skin or hair cleaning composition, or an all-purpose cleaning composition, wherein the amount of 4-tert-butyl-1-cyclohexanol is at least 0.05 by weight of the composition.

4. The composition of claim 3, wherein the skin or hair cleaning composition is a soap, a bath or shower gel, or a shampoo and the amount of 4-tert-butyl-1-cyclohexanol is 0.05 to 0.5% by weight of the composition.

* * * * *